United States Patent [19]

Villalta et al.

[11] Patent Number: 5,400,774
[45] Date of Patent: Mar. 28, 1995

[54] FOUR BLADE MEDICAL RETRACTOR

[76] Inventors: Josue J. Villalta, 11923 Discovery Cir., Indianapolis, Ind. 46236; Jean R. Passemard, 8 Rue Dela Tour Aux Saints, Crecy la Chapelle 77580, France

[21] Appl. No.: 149,066
[22] Filed: Nov. 8, 1993
[51] Int. Cl.⁶ .................................... A61B 17/02
[52] U.S. Cl. ................................................ 128/20
[58] Field of Search ................ 128/20, 3, 17, 18; 606/198, 191, 190

[56] References Cited

U.S. PATENT DOCUMENTS

| 447,761 | 3/1891 | Clough | 128/20 |
|---|---|---|---|
| 3,038,468 | 6/1962 | Raeuchle | 128/20 |
| 3,724,449 | 4/1973 | Gauthier | 128/20 |
| 3,750,652 | 8/1973 | Sherwin | |
| 4,130,113 | 12/1978 | Graham | |
| 4,667,657 | 5/1987 | Kulik et al. | |
| 4,991,566 | 2/1991 | Shulman et al. | 128/20 X |
| 5,081,983 | 1/1992 | Villalta et al. | |
| 5,183,032 | 2/1993 | Villalta et al. | |
| 5,284,129 | 2/1994 | Agbodoe et al. | 128/20 |
| 5,297,538 | 3/1994 | Daniel | 128/20 |
| 5,299,563 | 4/1994 | Seton | 128/20 |

FOREIGN PATENT DOCUMENTS

| 542744 | 4/1922 | France . |
|---|---|---|
| 1700 | 8/1884 | Germany . |
| 445162 | 2/1949 | Italy . |
| 464302 | 6/1951 | Italy . |
| 330629 | 6/1930 | United Kingdom . |

Primary Examiner—Richard J. Apley
Assistant Examiner—Donna L. Margolis
Attorney, Agent, or Firm—Woodard, Emhardt, Naughton Moriarty & McNett

[57] ABSTRACT

A medical retractor for holding open a body cavity. A base plate includes a pair of blades mounted and depending therefrom. A second plate is pivotally mounted to the base plate and has a second pair of blades slidably mounted thereto and depending therefrom. One of the blades is fixedly mounted whereas the three remaining blades are slidably mounted to the plates by arms having teeth engaging releasable locks on the plates. The second plate has a flat smooth surface defining the upper boundary of the retractor providing a snag free environment for the surgeon.

6 Claims, 5 Drawing Sheets

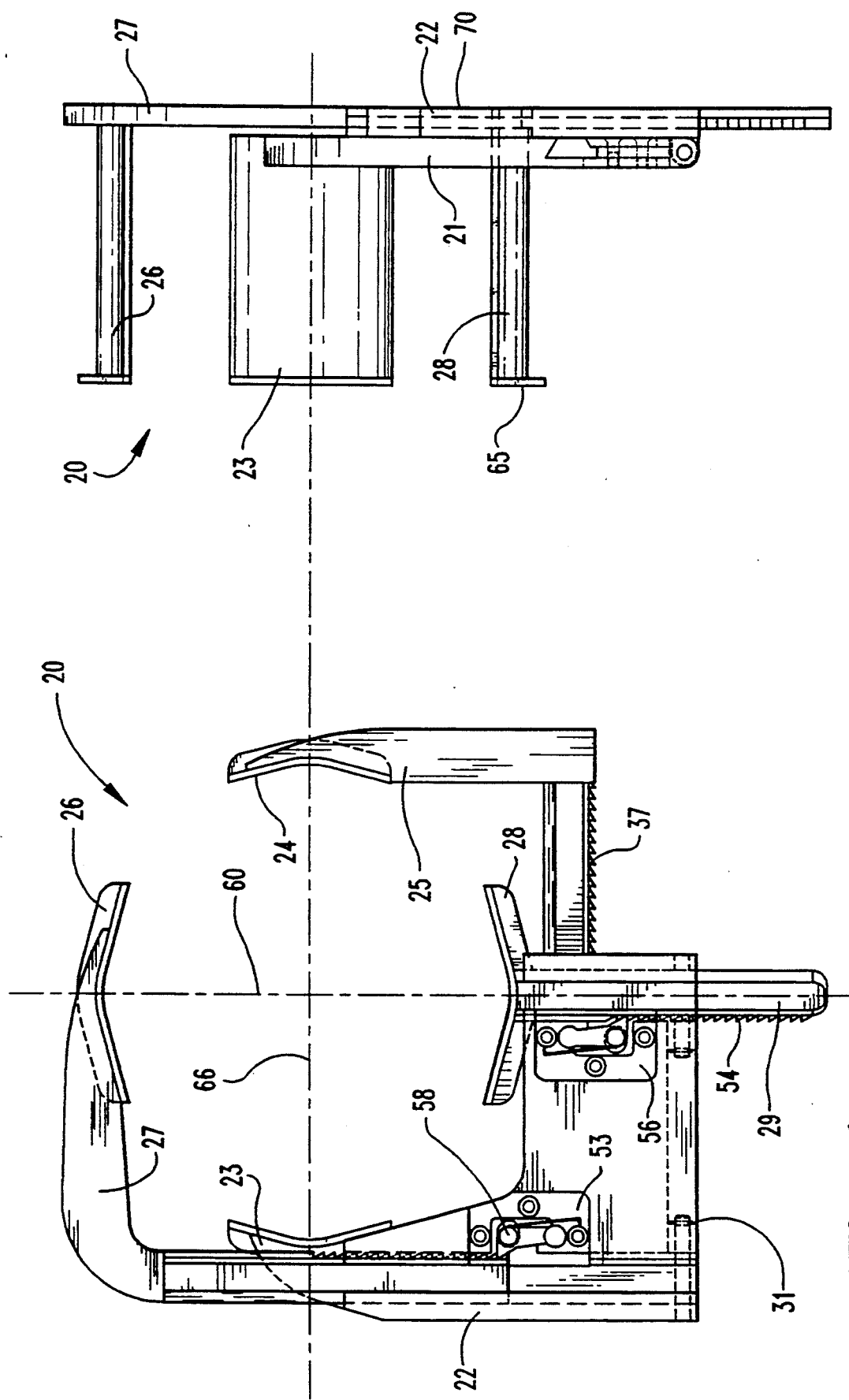

FOUR BLADE MEDICAL RETRACTOR

BACKGROUND OF THE INVENTION

1. Field of the Invention

This invention relates to devices for holding open a body cavity, particularly surgical openings.

2. Description of the Prior Art

In our U.S. Pat. Nos. 5,081,983 and 5,183,032, we have described different embodiments of a medical retractor for use in holding open body cavities in humans or animals. A variety of retractors have been provided in addition to the retractors described in our aforementioned patents. For example, various retractors are disclosed in the following U.S. Pat. Nos. 3,750,652 issued to Sherwin; 4,130,113 issued to Graham; and 4,667,657 issued to Kulik et al. The Sherwin retractor includes a pair of blades used to separate a patients knee with the blades being forcefully driven apart by means of a worm gear. The Graham patent discloses a plurality of flesh engaging blades arranged on a circular frame through which the surgeon operates. Finally, the Kulik et al. patent discloses a plurality of blades movable apart by means of a rod slidably mounted to the retractor frame. Foreign patents include Italian patents 445162 and 464302; British patent 330629; French patent 542744; and German patent 1700. The two Italian patents disclose a plurality of blades inserted into the cavity along with a stationary plate. Wing nuts or other members protrude outwardly from the retractor allowing the surgeon to possibly snag the surgical gloves thereon. The British patent discloses a plurality of blades mounted to a ring structure through which the surgeon examines the patient. The French patent also discloses a plurality of blades mounted to a ring shape frame. Finally, the German patent discloses an expandable retractor which utilizes a worm gear projecting to the side of the retractor frame.

Despite the many medical retractors provided to date, there is still need for a retractor which may be used by a surgeon without assistance from another with the surgeon being able to gradually open the wound, incision or body cavity to the desired size. Such a retractor and method of holding open the cavity must ensure that the retractor is stable relative to the patient and does not become accidentally dislodged.

A major disadvantage of the prior retractors is that the structures typically provide for a variety of fasteners and other elements which protrude outwardly above the retractor snagging the surgeons glove and surgical thread. Thus, there is a need for a retractor having a smooth flat upwardly facing surface with the retractor resting atop the patient in a stable manner while the blades protrude downwardly into the cavity. Disclosed herein is such a retractor.

SUMMARY OF THE INVENTION

One embodiment of the present invention is a medical retractor for holding open a body cavity comprising a first frame and a first blade mounted to the frame. The blade extends downwardly from the frame. A first arm is movably mounted to the frame. A second blade is mounted to the arm and extends downwardly from the frame. The second blade is spaced from the first blade a first distance along a first axis. A first adjustment device between the arm and the frame has a first condition whereat the second blade may be moved toward the first blade to allow insertion of the first blade and second blade into a body cavity and has a second condition whereat the second blade may be moved apart from the first blade and held positioning the first blade and second blade along the first axis at opposite cavity extremes. A second frame is movably mounted to the first frame and movable from a position away from the first frame to a position atop the first frame. The second frame includes a snag free surface facing upwardly when the second frame is positioned atop the first frame defining the upper boundary of the retractor. A third blade is mounted to the second frame. The third blade extends downwardly past the first frame and into the cavity when the second frame is atop the first frame. A second arm is movably mounted to the second frame. A fourth blade is mounted to the second arm and extends downwardly from the second frame. The fourth blade is spaced from the third blade a second distance along a second axis. A second adjustment device between the second arm and second frame has a third condition whereat the fourth blade may be moved in a first direction to allow insertion of the fourth blade into the cavity when the second frame is moved atop the first frame and has a fourth condition whereat the fourth blade may be moved in an opposite direction to the first direction and held holding the cavity open.

Another embodiment of the present invention is a method of holding open a surgical cavity comprising the steps of surgically providing an incision with a longitudinal axis with the incision having opposite extremes, inserting a first pair of blades into the incision, spreading the blades apart along an axis to opposite extremes, locking the blades in place at opposite extremes, inserting a third blade into the incision, inserting a fourth blade into the incision, spreading the third blade and fourth blade apart in a direction perpendicular to the axis, and locking the third blade and fourth blade in place.

It is an object of the present invention to provide a new and improved retractor and method of holding open a surgical cavity with the retractor being utilized by the surgeon without assistance from another.

Another object of the present invention is to provide such a retractor and method which maximizes the visual and operating area available within the cavity.

A further object of the present is to provide a medical retractor which does not include upwardly protruding elements such as fastening devices and instead, has a relatively flat upwardly facing surface.

Likewise, it is an object of the present invention to provide a retractor which remains relatively stationary in the body cavity and will not become accidentally dislodged.

Related objects and advantages of the present invention will be apparent from the following description.

BRIEF DESCRIPTION OF THE DRAWINGS

FIG. 1 is a top plan view of the retractor with the retractor blades protruding downwardly.

FIG. 2 is a left side view of the retractor of FIG. 1.

DESCRIPTION OF THE PREFERRED EMBODIMENT

Figure 3:
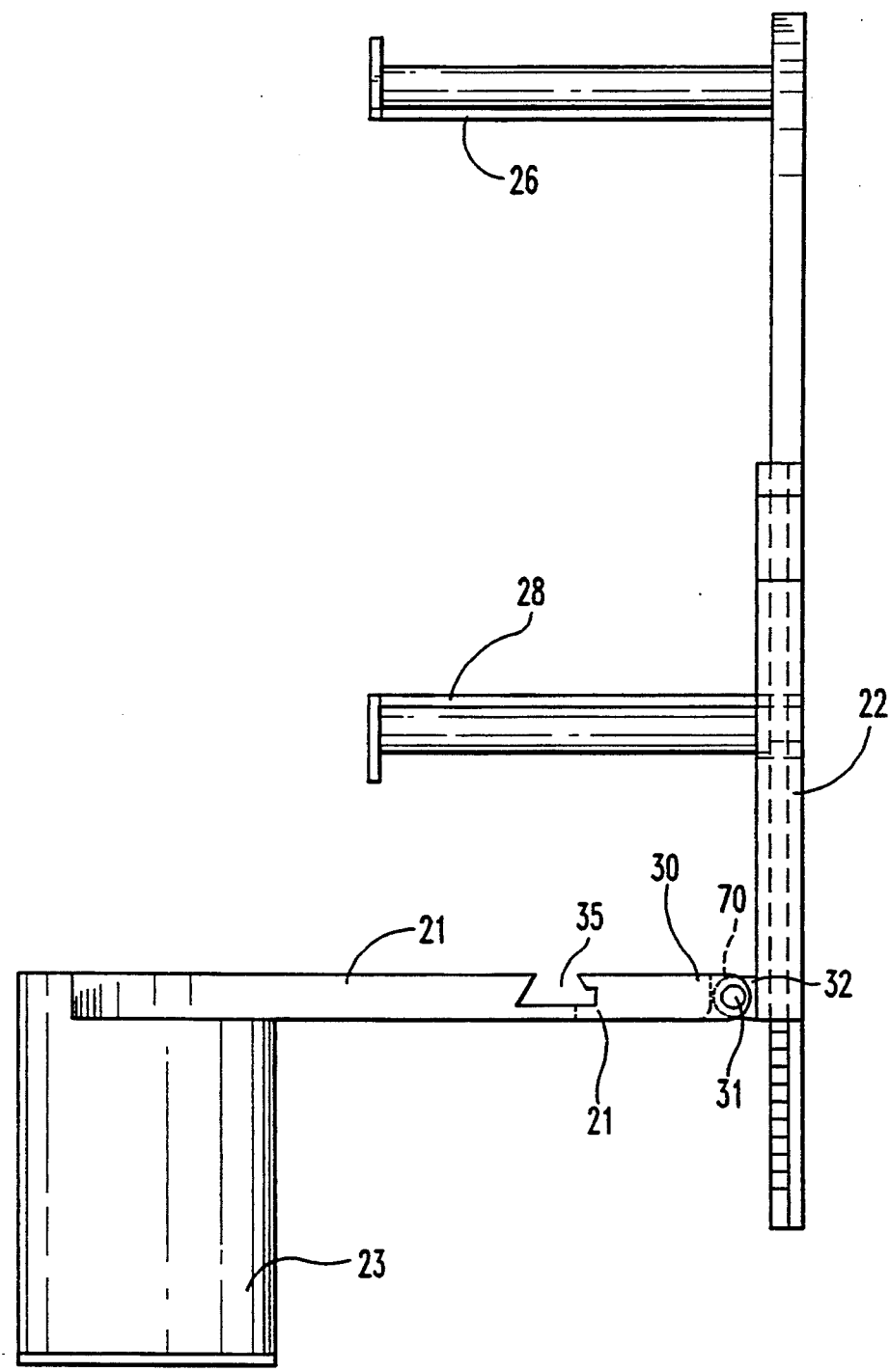
FIG. 3 is the stone view as FIG. 2 only showing a frame carrying one set of blades pivoted away from the second frame carrying a second pair of blades.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The retractor disclosed herein includes two articulating plates or frames held together by lateral hinges which allow the frames to be positioned at 180° flat over the patients abdomen. The frames hold the retractor abdominal blades.

Medical retractor 20 (FIGS. 1 and 2) includes a base frame 21 upon which is pivotally mounted a pivot frame 22. Frame 21 has a first blade 23 fixedly mounted thereto. A second blade 24 is mounted slidably to base frame 21 by means of an L-shaped arm 25. The second frame or pivot frame 22 includes a third blade 26 slidably mounted thereto by means of an L-shaped arm 27 whereas the fourth blade 28 is slidably mounted to frame 22 by means of arm 29. Arms 25, 27 and 29 include a plurality of teeth lockingly but releasably engaged by spring biased locks mounted to the frames to allow the blades to be moved apart and held stationary.

Figure 4:
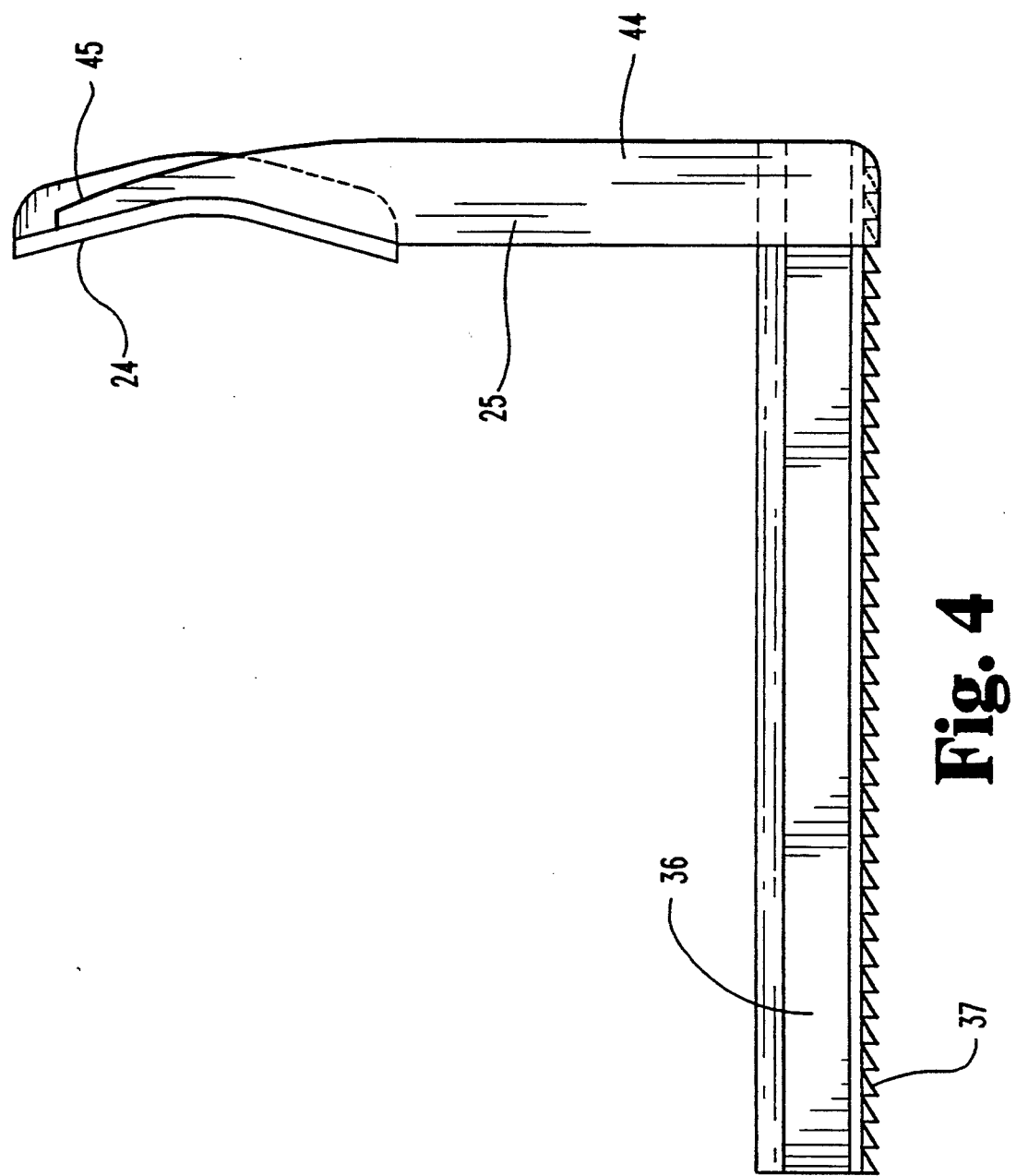
FIG. 4 is a plan view of the lateral blade and attached supporting arm.
Figure 7:
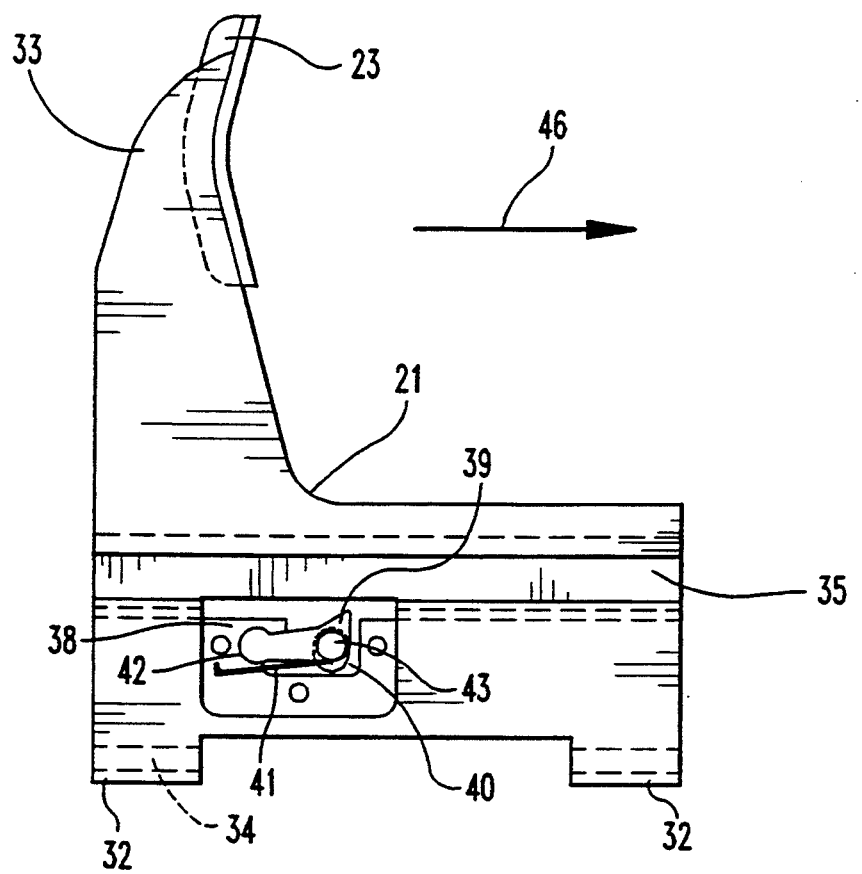
FIG. 7 is a top plan view of the base frame.
Figure 8:
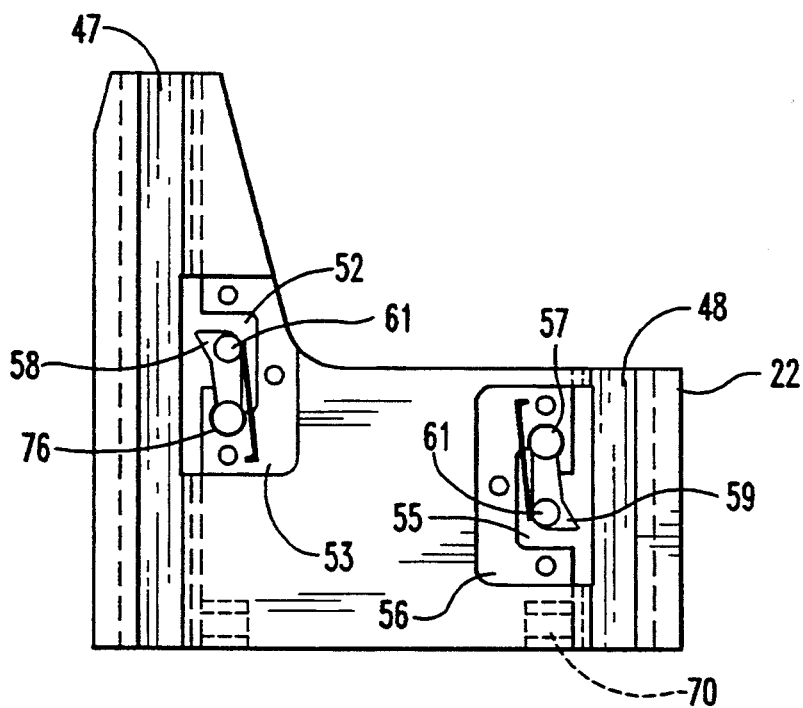
FIG. 8 is a top plan view of the pivot frame.

Base frame 21 (FIG. 7) has an L-shaped configuration with blade 23 fixedly mounted to the top or distal end 33 of the frame. A pair of bosses or flanges 32 are fixedly mounted to the opposite end of the frame with each flange having a through hole 34 through which pin 31 (FIG. 3) extends mounting the pivot frame 22 to frame 21. FIG. 3 illustrates pivot frame 22 pivoted upwardly and away from the base frame 21. The proximal end 30 of base frame 21 includes a plurality of flanges 70 (FIG. 8) pivotally mounted by means of pivot pins 31 to flanges 32 projecting outwardly from and integrally connected to pivot frame 22. A dove tail shaped channel 35 extends the length of the frame and opens upwardly to slidably receive arm portion 36 (FIG. 4) of arm 25. A plurality of teeth 37 are formed on arm portion 36 and project toward lock 38 (FIG. 7).

Lock 38, includes a wedge shaped projection 39 pivotally mounted within cavity 40 of frame 21. A wire spring 41 urges wedge shaped projection 39 to pivot in a counter clockwise direction about its end 42 pivotally retained within cavity 40. Opening 43 is formed in wedge shaped projection 39 and may be engaged by a pointed surgical instrument in order to pivot wedge shape projection 39 in a clockwise direction as viewed in FIG. 7 about end 42 thereby disengaging the lock from teeth 37.

Arm 25 (FIG. 4) is L-shaped having two arm portions 36 and 44 perpendicularly and integrally joked together with blade 24 fixedly molted to the outer distal end 45 of arm portion 44. The teeth 37 are arranged on arm portion 36 to allow blade 24 and the arm to move in the direction of arrow 46 (FIG. 7) even though wedge shaped projection 39 is in contact with teeth 37 thereby allowing the surgeon to pull blades 23 and 24 apart without releasing the lock 38. The teeth are, however, arranged to prevent movement of frame 24 in a direction opposite of arrow 46 unless wedge shaped projection 39 is pivoted in a clockwise direction as viewed in FIG. 7 in order to move the wedge shaped projection apart from the teeth and allow the blades to move together. In this manner, lock 38 provides an adjustment means having a first condition, that is, when wedge shaped projection 39 is moved apart from teeth 37, whereat blade 24 may be moved toward blade 23. Likewise, the lock is further operable having a second condition, that is, when the wedge shaped projection 39 is engaged with teeth 37 to allow blades 23 and 24 to be moved apart.

Figure 6:
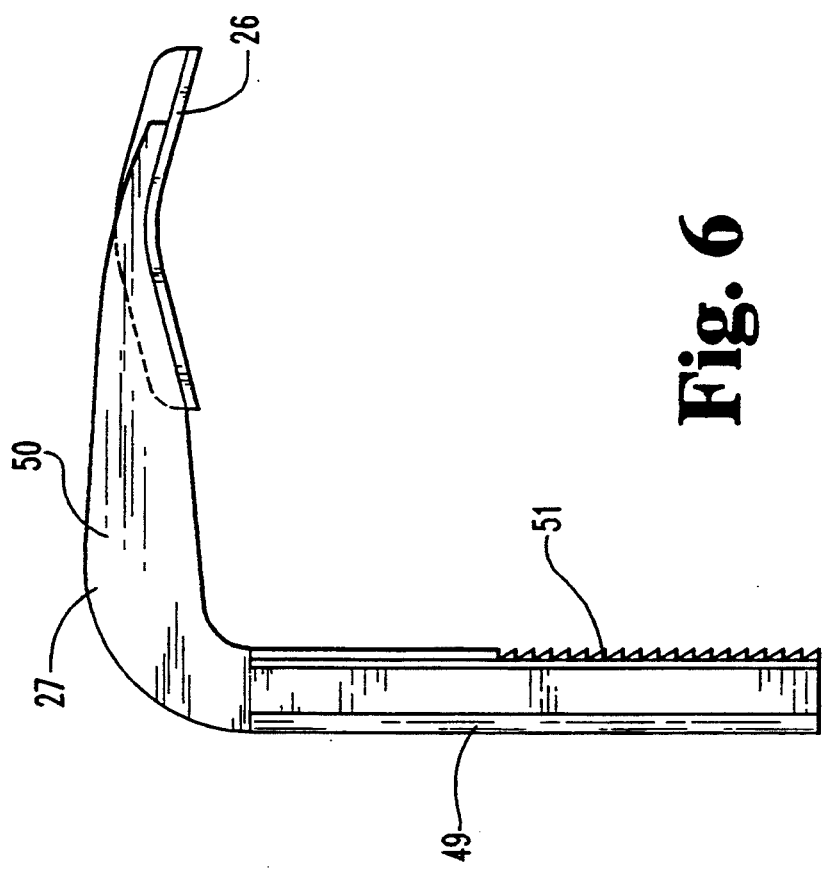
FIG. 6 is a plane view of the superior blade and supporting arm.
Figure 5:
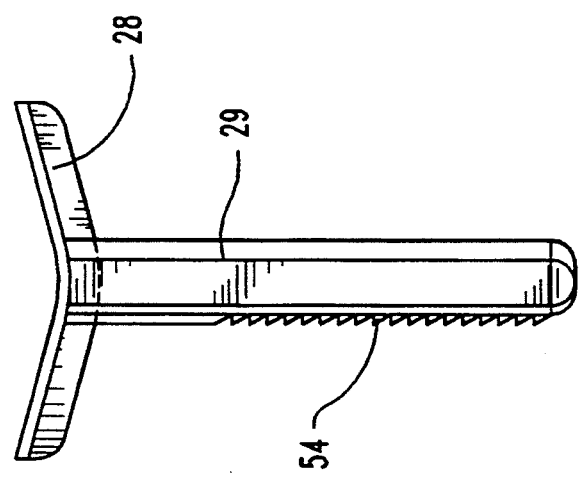
FIG. 5 is a plan view of the inferior blade and supporting arm.

The pivot frame 22 (FIG. 8) is also L-shaped and has a pair of dove tail channels 47 and 48 which slidably receive respectively arms 27 and 29 (FIG. 1) having fixedly mounted thereto blades 26 and 28. Channels 47, 48 and 35 have female dove tail configurations whereas arms 27, 29 and 25 have male dove tail configurations. Arm 27 (FIG. 6) has an L-shaped configuration having a pair of arm portions 49 and 50 perpendicularly and integrally joined together with arm portion 49 having teeth 51 projecting into cavity 52 of lock 53 provided on pivot frame 22. Arm 29 (FIG. 5) has a single straight member integrally joined to blade 28 with arm 29 having a plurality of teeth 54 projecting into lock cavity 55 of lock 56 provided on frame 22.

Locks 53 and 56 are constructed identically to lock 38 previously described. Thus, locks 53 and 56 provide a second adjustment means wherein blades 26 and 28 may be controllably moved together and/or apart. As viewed in FIG. 1, the teeth provided on arms 27 and 29 project inwardly to engage wedge shaped projections 58 and 59. Projections 58 and 59 are pivotally mounted within respective cavities 52 and 55 with projection 58 being pivotable apart from teeth 51 (FIG. 6) as the projection pivots in a clockwise direction as viewed in FIG. 8 about its mounted end 76. Likewise, wedge shaped projection 59 may be pivoted apart from teeth 54 when pivoted in a clockwise direction as viewed in FIG. 8 about its mounted end 57. Both locks 53 and 56 include wire springs normally urging the wedge shaped projections to engage teeth 51 and 54. Locks 53 and 56 provide a second adjustment memos which has a normally engaged condition, that is the wedge shaped projections 58 and 59 are engaged with teeth 51 and 54, but are yieldable to allow frames 26 and 28 to be moved in a direction apart along axis 60 (FIG. 1) extending centrally through blades 26 and 28. Once the blades are moved apart to the desired distance, then locks 53 and 56 prevent the blades from moving toward each other until either or both projections 58 and 59 are manually moved away from the engaged teeth. As in the case of lock 38, each wedge shaped projection 58 and 59 include an aperture 61 which may be engaged by a pointed instrument in order to pivot the wedge shaped projections apart from the teeth.

Blade 28 will now be described it being understood that a similar description applies to blades 23, 24 and 26. Blade 28 has a sheet like main body having a generally concave configuration which faces the oppositely aligned blade 26. Blade 28 (FIG. 2) extends downwardly from frame 22 and includes an outwardly turned bottom flange 65 for engaging the inner tissue of the cavity preventing accidental dislodgement of the blade from the cavity.

Blades 23 and 24 (FIG. 1) have a second axis 66 extending centrally therethrough with axis 66 being located perpendicularly relative to axis 60. Blades 23 and 24 are each concave with blade 23 being aligned with and facing blade 24. Likewise, blades 26 and 28 are concave with blade 26 being aligned with and facing blade 28.

The medical retractor 20 is operable to hold open a body cavity and includes a first frame 21 and a second frame 22 movably mounted to the first frame. Frame 22 is movable from a position away from frame 21 as shown in FIG. 3 to a position atop, that is adjacent, to the first frame as shown in FIG. 2. Notably, the second frame 22 includes a snag free surface 70 which faces upwardly when the second frame 22 is positioned atop the first frame 21 defining the upper boundary of the retractor thereby providing a snag free environment for the surgeons gloves and the surgical thread. Blades 24, 26 and 28 along with their connected arms are slidably mounted to the frames whereas the remaining blade 23 is fixedly mounted to frame 21. Thus, blades 24, 26 and 28 are removably mounted to their associated frames to facilitate cleaning as well as the surgical method to be described later in the specification. As a result of the slidable mounting feature of each blade 24, 26 and 28, each of the three blades are positionable on the frames independently of each other to control the distances between the mutually facing blades. Blades 23 and 24 extend downwardly from frame 21 when the frame is positioned atop a patient and the blades are extended into the body cavity. Likewise, blades 26 and 28 extend downwardly from frame 22 and past frame 21 into the body cavity when frame 22 is pivoted atop and adjacent frame 21.

Once the surgeon has made the incision at a place such as the abdominal cavity, the surgeon positions or rests frame 21 atop the body adjacent the incision with blades 23 and 24 positioned together. Blades 23 and 24 are then inserted into the surgical wound and pulled apart along axis 66 which is aligned with the longitudinal axis of the incision. Blade 24 is moved apart from blade 23 along axis 66 by pulling arm 25 outwardly until blades 23 and 24 are located at the opposite extremes of the incision. Blades 23 and 24 are automatically locked in place at the opposite extremes since blade 23 is fixedly mounted to frame 21 and since lock 38 is operable to hold arm 25 in its outward position.

The surgeon then inserts blade 26 all the way into channel 47 of pivot frame 22. Plate 22 is then pivoted 180° downward until frame 22 is atop and adjacent frame 21 as depicted in FIG. 2. Thus, blade 26 is inserted into the incision between the opposite extremes of the incision. At this time, the surgeon pulls arm 27 outwardly, thereby moving blade 26 outwardly along axis 60 causing the cavity to open. The surgeon is therefore able to pack the intestines away with appropriate material prior to inserting blade 28 into the body cavity.

Blade 28 is then inserted into the abdominal cavity by aligning arm 29 with channel 48. The arm is inserted into the channel with blade 28 then being moved along axis 60 in a direction away from blade 26 retaining the packing material and intestines away from the surgical field. The abdominal cavity is thus completely open providing an optimal view of the pelvic/abdominal area in which the surgeon needs to operate.

To remove the retractor, the surgeon manually pivots each lock in order to be in order to be able to slide each particular retractor blade in a reverse fashion thereby allowing the blades and associated frames to be lifted from the cavity.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical retractor for holding open a body cavity comprising:

a first frame;

a first blade mounted to said frame, said blade extending downwardly from said frame;

a first arm movably mounted to said frame;

a second blade mounted to said arm and extending downwardly from said frame, said second blade spaced from said first blade a first distance along a straight first axis;

first adjustment means between said arm and said frame and having a first condition whereat said second blade may be moved toward said first blade only along said first axis to allow insertion of said first blade and said second blade into a body cavity and having a second condition whereat said second blade may be moved only along said first axis apart from said first blade and held positioning said first blade and said second blade along said first axis at opposite cavity extremes;

a second frame movably mounted to said first frame and movable from a position apart from said first frame to a position atop said first frame, said second frame including a snag free surface facing upwardly when said second frame is positioned atop said first frame defining the upper boundary of the retractor;

a third blade mounted to said second frame, said third blade extending downwardly past said first frame and into said cavity when said second frame is atop said first frame;

a second arm movably mounted to said second frame;

a fourth blade mounted to said second arm and extending downwardly from said second frame, said fourth blade spaced from said third blade a second distance along a straight second axis; and, second adjustment means between said second arm and said second frame and having a third condition whereat said fourth blade may be moved independent of said second blade and only along said second axis in a first direction to allow insertion of said fourth blade into said cavity when said second frame is moved atop said first frame and having a fourth condition whereat said fourth blade may be moved only along said second axis in an opposite direction to said first direction and held holding said cavity open, said first adjustment means and said second adjustment means located entirely beneath said snag free surface when said snag free surface faces upwardly, said snag free surface forming the entire upper surface of said retractor.

2. The retractor of claim 1 wherein:

said first frame includes a first edge portion and said second frame includes a second edge portion with said second edge portion pivotally mounted to said first edge portion;

said second blade, third blade and fourth blade are removably mounted to said second frame.

3. The retractor of claim 1 wherein:

said first arm and second arm are slidably mounted respectively to said first frame and said second frame, and said second frame is pivotally mounted to said first frame about a pivot axis and movable from a first position apart from said first frame to a second position atop said first frame, said second frame has a guide channel into which said second arm may be inserted when said second frame is in said first position.

4. The retractor of claim 5 wherein:

said third blade is slidably mounted to said second frame.

5. A medical retractor for holding open a surgical cavity comprising:

a base;

a first blade mounted to said base;

a second blade slidably mounted to said base and movable to and from said first blade along a straight first axis;

a frame pivotally mounted to said base and movable from a remote position relative to said base to a position atop said base;

a third blade mounted to said frame;

a fourth blade slidably mounted to said frame and movable to and from said third blade along a straight second axis perpendicularly arranged to said first axis;

first means to releasably hold said second blade apart from said first blade a first distance and second means to releasably hold said fourth blade apart from said third blade a second distance holding said cavity open when all blades are inserted therein, said first means and said second means located so said base and frame form a snag free upwardly facing surface, said snag free upwardly facing surface forming the entire upper surface of said retractor.

6. The retractor of claim 5 wherein:

said third blade is slidably mounted to said frame and projects with said fourth blade downwardly into the cavity past said base when said second frame is atop said base;

and further comprising a first arm slidably mounted to said base having said second blade mounted thereon;

a second arm slidably mounted to said frame having said third blade mounted thereon;

a third arm slidably mounted to said frame having said fourth blade mounted thereon; and wherein;

said first means and said second means includes a plurality of spring biased locks mounted on said base and said frame;

said first arm, said second arm, and said third arm include teeth engageable with said locks.

* * * * *

UNITED STATES PATENT AND TRADEMARK OFFICE
CERTIFICATE OF CORRECTION

PATENT NO. : 5,400,774

DATED : March 28, 1995

INVENTOR(S) : Josue J. Villalta and Jean Robert Passemard

It is certified that error appears in the above-identified patent and that said Letters Patent is hereby corrected as shown below:

Column 2, line 61 delete "stone" and insert --same--.
Column 3, line 63 delete "joked" and insert --joined--.
Column 3, line 64 delete "molted" and insert --mounted--.
Column 4, line 46 delete "memos" and insert --means--.
Column 7, line 13 delete "5" and insert --3--.

Signed and Sealed this

Thirteenth Day of June, 1995

Attest:

BRUCE LEHMAN

*Attesting Officer*   *Commissioner of Patents and Trademarks*